United States Patent
Knoop et al.

(10) Patent No.: US 6,680,414 B2
(45) Date of Patent: Jan. 20, 2004

(54) PROCESS FOR THE HYDROGENATION OF HYDROFORMYLATION MIXTURES

(75) Inventors: Cord Knoop, Haltern (DE); Bernhard Scholz, Marl (DE); Alfred Kaizik, Marl (DE); Dietmar Gubisch, Marl (DE); Joachim Schuler, Marl (DE); Walter Tötsch, Marl (DE); Wilfried Büschken, Haltern (DE)

(73) Assignee: Oxeno Olefinchemie GmbH, Marl (DE)

( * ) Notice: Subject to any disclaimer, the term of this patent is extended or adjusted under 35 U.S.C. 154(b) by 0 days.

(21) Appl. No.: 10/014,517

(22) Filed: Dec. 14, 2001

(65) Prior Publication Data

US 2003/0114718 A1 Jun. 19, 2003

(30) Foreign Application Priority Data

Dec. 14, 2001 (DE) .......................... 100 62 448

(51) Int. Cl.[7] .......................... C07C 27/00; C07C 45/00
(52) U.S. Cl. .................. 568/830; 568/861; 568/878; 568/429; 568/444; 568/451; 568/772; 568/798; 568/814
(58) Field of Search ................. 568/883, 429, 568/444, 451, 772, 798, 814, 830, 861, 878

(56) References Cited

U.S. PATENT DOCUMENTS

| | | | |
|---|---|---|---|
| 2,760,994 A | | 8/1956 | Gwynn |
| 2,771,493 A | | 11/1956 | Jacks et al. |
| 2,809,220 A | | 10/1957 | Mertzweiller et al. |
| 4,263,449 A | * | 4/1981 | Saito et al. |
| 4,401,834 A | | 8/1983 | King |
| 4,517,395 A | | 5/1985 | Obenaus et al. |
| 5,059,710 A | | 10/1991 | Abatjoglou et al. |
| 5,306,848 A | * | 4/1994 | Vargas |
| 6,015,298 A | | 1/2000 | Linhart |
| 6,184,424 B1 | | 2/2001 | Bueschken et al. |
| 6,239,318 B1 | | 5/2001 | Schuler et al. |
| 6,303,535 B1 | | 10/2001 | Scholz et al. |
| 6,331,657 B1 | | 12/2001 | Kaizik et al. |
| 6,403,836 B2 | | 6/2002 | Kaizik et al. |
| 6,407,295 B1 | | 6/2002 | Kaizik et al. |

FOREIGN PATENT DOCUMENTS

| | | |
|---|---|---|
| DE | 198 42 370 | 3/2000 |
| DE | 199 33 348 | 2/2001 |
| EP | 0987 241 A1 | 3/2000 |
| GB | 784359 | 10/1957 |
| GB | 808336 | 2/1959 |
| GB | 2 142 010 | 1/1985 |

OTHER PUBLICATIONS

J. Falbe, "New Synthesis with Carbon Monoxide", Springer–Verlag, Heidelbert–New York, p. 99ff, 1980.
Kirk–Othmer, Encyclopedia of Chemical Technology, vol. 17, 4th Edition, John Wiley & Sons, pp. 902–919, 1996.
J. Falbe, loc. cit, Kirk–Othmer, loc. cit., pp. 164–165, 174–175.

* cited by examiner

Primary Examiner—Samuel Barts
Assistant Examiner—Sikarl A. Witherspoon
(74) Attorney, Agent, or Firm—Oblon, Spivak, McClelland, Maier & Neustadt, P.C.

(57) ABSTRACT

The present invention provides a process, which includes:
  in a homogeneous liquid phase including water, and over a fixed-bed catalyst,
  continuously hydrogenating at least one hydroformylation product obtained from a hydroformylation of one or more $C_{4-16}$ olefins to produce at least one output mixture;
  wherein the fixed-bed catalyst includes at least one element of transition group eight of the Periodic Table of the Elements;
  wherein the output mixture includes at least one corresponding alcohol and from 0.05 to 10% by weight of water;
  and wherein in a steady-state operation of the process, from 3 to 50% more hydrogen is fed to the hydrogenation than is consumed by the hydrogenation.

20 Claims, No Drawings

PROCESS FOR THE HYDROGENATION OF HYDROFORMYLATION MIXTURES

BACKGROUND OF THE INVENTION

1. Field of the Invention

The invention relates to a process for the hydrogenation of hydroformylation mixtures, i.e. for preparing alcohols by hydrogenation of aldehydes in the liquid phase in the presence of water.

2. Discussion of the Background

Alcohols can be obtained by catalytic hydrogenation of aldehydes which have been obtained, for example, by hydroformylation of olefins. Large quantities of alcohols are used as solvents and as intermediates for preparing many organic compounds. Important downstream products of alcohols are plasticizers and detergents.

It is known that aldehydes can be catalytically reduced with hydrogen to form alcohols. Catalysts which include at least one metal of groups 1b, 2b, 6b, 7b and/or 8 of the Periodic Table of the Elements are frequently used. The hydrogenation of aldehydes can be carried out continuously or batchwise using pulverulent or palletized/shaped catalysts in the gas or liquid phase.

For the industrial production of alcohols by hydrogenation of aldehydes from the oxo process (hydroformylation of olefins), preference is given, especially in the case of large-volume products, to continuous gas- or liquid-phase processes using catalysts located in a fixed bed.

Compared to gas-phase hydrogenation, liquid-phase hydrogenation has a more favorable energy balance and gives a higher space-time yield. As the molar mass of the aldehyde to be hydrogenated increases, i.e. as the boiling point increases, the advantage of the more favorable energy balance increases. Higher aldehydes having more than 7 carbon atoms are therefore preferably hydrogenated in the liquid phase.

However, hydrogenation in the liquid phase has the disadvantage that, owing to the high concentrations of both aldehydes and alcohols, the formation of high boilers via subsequent and secondary reactions is promoted. Thus, aldehydes can more readily undergo aldol reactions (addition and/or condensation) and form hemiacetals or acetals with alcohols. The acetals or hemiacetals formed can undergo elimination of alcohol or water, respectively, to form enol ethers which are hydrogenated under the reaction conditions to form the saturated ethers. These secondary by-products thus reduce the yield. The by-products referred to as high boilers can at best sometimes be redissociated in downstream plants to give products of value, e.g. starting aldehydes and target alcohols.

Industrial aldehyde mixtures which are used for the hydrogenation frequently already contain varying concentrations of high boilers.

Hydroformylation of olefins in the presence of cobalt catalysts gives crude aldehydes which contain esters of formic acid (formates) and also aldol products, high esters and ethers as well as acetals as high boilers. If these mixtures are hydrogenated in the gas phase, the major part of the high boilers can be separated off in the vaporizer and worked up in a separate process step to give products of value.

In contrast, in the case of the liquid-phase hydrogenation, the high boilers remain in the reactor feed. They are mostly hydrogenated in the hydrogenation step, so that it is no longer possible to obtain a product of value from them.

In U.S. Pat. No. 5,059,710, the yield of alcohols in the hydrogenation of crude aldehydes is increased by redissociating part of the high boilers by means of water at elevated temperature to form aldehydes or alcohols in a process step upstream of the hydrogenation. Hydrolysis and hydrogenation are therefore separate process steps; nothing is said about the water content of the mixture to be hydrogenated.

A similar process is disclosed in U.S. Pat. No. 4,401,834. Here too, the cleavage of high boilers is carried out in the presence of water prior to the actual hydrogenation step.

GB 2 142 010 claims a process for the hydrogenation of crude aldehydes having from 6 to 20 carbon atoms which contain high boilers and small amounts of sulfur compounds to give the corresponding saturated alcohols. The hydrogenation is carried out in two reactors connected in series. The first reactor contains an $MoS_2/C$ catalyst and the second reactor contains an $Ni/Al_2O_3$ catalyst. The hydrogenation in both reactors is carried out with addition of up to 10% of water vapor, based on the feed stream, in a temperature range of from 180 to 260° C. and a hydrogen partial pressure of from 150 to 210 bar using a large excess of hydrogen. In the examples, this is so large that the added water is present virtually only in the gas phase. The object of this process is to suppress the formation of hydrocarbons by hydrogenolysis of the alcohols. Nothing is said about an increase or decrease in high boilers and formates in the hydrogenation.

U.S. Pat. No. 2,809,220 describes a liquid-phase hydrogenation of hydroformylation mixtures in the presence of water. The catalysts used are sulfur-containing catalysts. The hydrogenation is carried out in a pressure range of from 105 to 315 bar and a temperature range from 204 to 315° C. in the presence of from 1 to 10% of water, based on starting material. To keep the added water in the gas phase, a large excess of hydrogen (from 892 to 3566 standard $m^3$ of hydrogen per $m^3$ of starting material) is used. As regards the high excess of hydrogen, reference is made to the discussion of GB 2 142 010. A further disadvantage of this process is the high specific energy consumption.

A further process for the hydrogenation of hydroformylation mixtures is disclosed in DE 198 42 370. This document describes the hydrogenation of hydroformylation mixtures in the liquid phase over copper-, nickel- and chromium-containing supported catalysts. Depending on the process used for preparing the hydroformylation mixtures (rhodium or cobalt processes), these mixtures contain water. The process disclosed is designed for the selective hydrogenation of the aldehydes to alcohols, without hydrogenation of the olefins which have remained unreacted in the hydroformylation, i.e. the high boilers (mostly acetals) are not converted into the useful product. This is economically unfavorable and is therefore capable of improvement.

Since the known processes are not economically optimal (e.g., low capital cost, high product yield and low energy consumption), it is desirable to develop a new process for the hydrogenation of aldehydes or aldehyde mixtures to the corresponding saturated alcohols, which process combines the advantages of gas-phase hydrogenation (high selectivity) with those of liquid-phase hydrogenation (low energy consumption, high space-type yield).

SUMMARY OF THE INVENTION

It is an object of the present invention to provide a new process for the hydrogenation of aldehydes or aldehyde mixtures to the corresponding saturated alcohols, which has a low capital cost, high product yield and low energy consumption.

Another object of the invention is to provide a new process for the hydrogenation of aldehydes or aldehyde mixtures to the corresponding saturated alcohols, which process combines the advantages of gas-phase hydrogenation (high selectivity) with those of liquid-phase hydrogenation (low energy consumption, high space-type yield).

These and other objects may be accomplished with the present invention, the first embodiment of provides a process, which includes:

in a homogeneous liquid phase including water, and over a fixed-bed catalyst, continuously hydrogenating at least one hydroformylation product obtained from a hydroformylation of one or more $C_{4-16}$ olefins to produce at least one output mixture;

wherein the fixed-bed catalyst includes at least one element of transition group eight of the Periodic Table of the Elements;

wherein the output mixture includes at least one corresponding alcohol and from 0.05 to 10% by weight of water;

and wherein in a steady-state operation of the process, from 3 to 50% more hydrogen is fed to the hydrogenation than is consumed by the hydrogenation.

DESCRIPTION OF THE PREFERRED EMBODIMENTS

Various other objects, features and attendant advantages of the present invention will be more fully appreciated as the same becomes better understood from the following detailed description of the preferred embodiments of the invention.

It has been found that the yield of alcohols in the liquid-phase hydrogenation of aldehydes or industrial aldehyde mixtures is increased when the hydrogenation is carried out in the presence of water and the water is present mainly in the liquid phase under the reaction conditions and no separate liquid water phase is formed.

The invention accordingly provides a process for the continuous hydrogenation of reaction mixtures from the hydroformylation of olefins having from 4 to 16 carbon atoms in the homogeneous liquid phase over fixed-bed catalysts including at least one element of transition group eight of the Periodic Table of the Elements, wherein the homogeneous liquid phase of the output from the reactor still contains from 0.05 to 10% by weight of water and, in steady-state operation of the process, from 3 to 50% more hydrogen is fed in than is consumed by the hydrogenation.

The group system herein is in line with the earlier IUPAC recommendation (see, Periodisches System der Elemente (Periodic Table of the Elements), Verlag Chemie, Weinheim, 1985, the entire contents of which are hereby incorporated by reference. Transition group eight includes Fe, Ru, Os, Co, Rh, Ir, Ni, Pd and Pt.

The process of the invention has a series of advantages. In the hydrogenation of pure aldehydes in the liquid phase in the presence of homogeneously dissolved water, the yields and selectivities correspond to those of gas-phase hydrogenations, but the energy consumption is appreciably lower.

If aldehydes or aldehyde mixtures contain formates and high boilers, with the latter including predominantly aldol products and acetals, are hydrogenated in the liquid phase in the presence of water, formates (formic acid esters) are converted virtually completely into alcohols and high boilers are partly converted into alcohols. As a result, the amount of alcohol formed is greater than the amount equivalent to the amount of aldehyde in the feed mixture.

In the hydrogenation of pure aldehydes or aldehydes low in high boilers by the process of the invention, high boiler formation in the hydrogenation is significantly reduced and the selectivity of the hydrogenation is improved significantly as a result. To obtain the selectivity- and yield-increasing action of the water, it is necessary for the water to be present in the liquid phase. The presence of water in the gas phase is therefore not decisive.

The starting materials for the preparation of the aldehydes or the reaction mixture by hydroformylation are olefins or mixtures of olefins having from 4 to 16, preferably from 6 to 12, carbon atoms and terminal or internal C—C double bonds, e.g. 1-butene, 2-butene, isobutene, 1- or 2-pentene, 2-methyl-1-butene, 2 methyl-2-butene, 3-methyl-1-butene, 1-, 2- or 3-hexene, the C6-olefin mixture obtained in the dimerization of propene (dipropene), heptenes, 2- or 3 methyl-1-hexene, octenes, 2-methylheptenes, 3-methylheptenes, 5-methyl-2-heptene, 6-methyl-2-heptene, 2-ethyl-1-hexene, the mixture of isomeric C8-olefins obtained in the dimerization of butenes (dibutene), nonenes, 2- or 3-methyloctenes, the C9-olefin mixture obtained in the trimerization of propene (tripropene), decenes, 2-ethyl-1-octene, dodecenes, the C12-olefin mixture obtained in the tetramerization of propene or the trimerization of butenes (tetrapropene or tributene), tetradecenes, pentadecenes, hexadecenes, the C16-olefin mixture obtained in the tetramerization of butenes (tetrabutene) and also olefin mixtures prepared by cooligomerization of olefins having different numbers of carbon atoms (preferably from 2 to 4), optionally after separation into fractions having an identical or similar chain length by distillation. It is likewise possible to use olefins or olefin mixtures produced by Fischer-Tropsch synthesis and also olefins obtained by oligomerization of ethene or olefins obtainable via methathesis reactions. Preferred starting materials for the preparation of the hydroformylation mixtures are C8-, C9-, C12-, C15- or C16-olefins and/or mixtures thereof.

The olefins are hydroformylated in a customary fashion and then represent the starting materials for the hydrogenation process of the invention. The hydroformylation is generally carried out using rhodium or cobalt catalysts with or without additives to stabilize the complex, e.g. organic phosphines or phosphites. The temperatures and pressures can, depending on the catalyst or olefin, be varied within wide limits. A description of the hydroformylation of olefins may be found, for example, in J. Falbe, New Syntheses with Carbon Monoxide, Springer-Verlag, Heidelberg-New York, 1980, page 99 ff., and also in Kirk-Othmer, Encyclopedia of Chemical Technology, volume 17, 4th edition, John Wiley & Sons, pages 902 to 919 (1996). The entire contents of each of the aforementioned references is hereby incorporated reference.

In the process of the invention, preference is given to using hydroformylation mixtures prepared from C8-, C12-olefins or C8-, C12-olefin mixtures.

The amount of aldehyde in the feed to the reactor can be limited to concentrations of 1–35% by weight, preferably 5–20% by weight. These ranges expressly include all values and subranges therebetween, including 2, 3, 7, 9, 10, 11, 12, 14, 15, 18, 22, 25, 29, 30, 31, and 34% by weight.

The reaction mixtures from the hydroformylation are advantageously firstly freed of the catalyst. If a cobalt catalyst has been used, this can be achieved by depressurization, oxidation of the cobalt carbonyl compounds remaining in the hydroformylation mixture in the presence of water or aqueous acid and separation of the aqueous phase. Cobalt removal processes are well known, cf., for example, J. Falbe, loc. cit., Kirk-Othmer, loc. cit., 164, 175, BASF process, the entire contents of which are hereby incorporated by reference.

If a rhodium compound is used as hydroformylation catalyst, it can, for example, be separated off as distillation residue by means of thin film evaporation.

The reaction mixtures from the cobalt-catalyzed hydroformylation which have been freed of the hydroformylation catalyst generally include from 3 to 40% by mass, usually from 5 to 30% by mass, of low boilers, mainly unreacted olefins, together with the corresponding saturated hydrocarbons and also from 0.05 to 5% by mass of water, from 30 to 90% by mass of aldehydes, from 5 to 60% by mass of alcohols, up to 10% by mass of formates of these alcohols and from 3 to 15% by mass of high boilers.

The above ranges independently include all values and subranges therebetween, including 4, 10, 15, 20, 25, 29, 31, and 35% by mass of low boilers; 0.07, 0.1, 0.5, 0.9, 1, 2, 3, and 4% by mass of water; 31, 33, 35, 40, 45, 50, 55, 60, 65, 70, 75, 80, 85 and 89% by mass of aldehydes; 6, 10, 15, 20, 25, 30, 35, 40, 45, 50, 55 and 57% by mass of alcohols; 1, 2, 3, 4, 5, 6, 7, 8, and 9% by mass of formates of these alcohols; and 4, 5, 6, 7, 8, 9, 10, 11, 12, 13 and 14% by mass of high boilers.

In contrast to the cobalt-catalyzed hydroformylation, the reaction mixtures from the rhodium-catalyzed hydroformylation contain virtually no water. In this case, water has to be introduced in appropriate amounts.

However, it must be emphasized that the process of the invention can also be carried out using hydroformylation mixtures whose composition does not correspond to that indicated above in this or any other respect. Thus, for example, the hydrocarbons (olefins and paraffins) can be separated off from the hydroformylation mixture prior to the hydrogenation.

The hydrogenation of aldehydes by means of the process of the invention in the liquid phase in the presence of water can be carried out using palletized/shaped catalysts located in a fixed bed. These may include one or more metals of groups 1b, 2b, 6b, 7b and/or 8 of the Periodic Table, in particular nickel, copper and chromium. It is possible to use catalysts on oxidic supports such as aluminum oxide, silicon oxide, titanium oxide, aluminosilicates or support-free catalysts. Support-free catalysts generally include from about 0.2 to 30% by weight of nickel, from 0.3 to 40% by mass of copper and from 18 to 40% by mass of chromium. The catalysts can further include up to 20% by mass of basic substances such as alkali metal or alkaline earth metal oxides or hydroxides, and also other inert or property-modifying materials in the same amounts, for example graphite. The catalysts used according to the invention do not contain any sulfur or sulfur compounds.

Preferred catalysts in the process of the invention for the hydrogenation of aldehydes to alcohols are supported catalysts. The catalysts contain from 0.3 to 15% by weight of copper and from 0.3 to 15% by weight of nickel and also, as activators, from 0.05 to 3.5% by weight of chromium and advantageously from 0 to 1.6% by weight of an alkali metal. The support material preferably includes aluminum oxide and/or silicon oxide.

The catalysts are advantageously used in a form in which they offer a low flow resistance, e.g. in the form of granules, pellets or shaped bodies such as tablets, cylinders, spheres, extrudates or rings. They are advantageously activated prior to use by heating in a stream of hydrogen at, for example, from 140 to 250° C. if they are not reduced in the hydrogenation reactor. For example, a method of reduction by means of hydrogen in the presence of a liquid phase is described in DE 199 33 348.3, the entire contents of which are hereby incorporated by reference.

According to a preferred embodiment of the invention, the hydrogenation is carried out in the homogeneous liquid phase in the presence of water, with the homogeneous liquid phase of the output from the reactor containing from 0.05 to 10% by weight, preferably from 0.5 to 8% by weight, particularly preferably from 1 to 5% by weight, of water. The stated water contents are to be regarded as independent of consumption of water by chemical reactions and of discharge of water together with the offgas from the hydrogenation. Under the reaction conditions of the hydrogenation, the water is present mainly in the organic starting material/product phase and only a small proportion is present in the gas phase. In the ideal case, no water is present in the gas phase. A further, liquid water phase is not present. The specific amount of water in the organic phase is determined by the solubility of water, the vapor pressure of water and the phase ratio (gas to liquid) under the reaction conditions. The minimum amount of water necessary is that which is consumed in the hydrolysis of formic acid esters, acetals, enol ethers, aldol condensation products and any other hydrolyzable substances. If the starting material contains large proportions of hydrolyzable compounds, it may be necessary to add only part of the required water at the beginning in order to prevent formation of a second aqueous phase in the hydrogenation reactor. The other part is fed in during the hydrogenation as a function of the water consumption. When using only one reactor, this may be carried out at one or more points on the reactor; when using a plurality of reactors connected in series, advantageously before the individual reactors. To prevent any aldehyde protected as hemiacetal or acetal from escaping hydrogenation, the output from the hydrogenation (in the case of a plurality of reactors, from the last reactor) may still contain water. The water content of the homogeneous liquid phase of the output from the reactor can be from 0.05 to 10% by mass, preferably from 0.5 to 8% by mass. These ranges include all values and subranges therebetween, including 0.075, 0.1, 0.4, 0.6, 0.9, 1, 1.1, 2, 3, 4, 5, 6, 7, and 9%.

Various process variants can be chosen for the process of the invention. It can be carried out adiabatically or virtually isothermally, i.e. with a temperature increase of less than 10° C., in one or more stages. In the latter case, all reactors, advantageously tube reactors, are operated adiabatically or virtually isothermally or one or more are operated adiabatically and the others are operated virtually isothermally. It is also possible for the aldehydes or aldehyde mixtures to be hydrogenated in the presence of water in a single pass or with product recirculation.

The process of the invention is carried out in cocurrent in the trickle phase or preferably in the liquid phase in three-phase reactors, and the hydrogen is finely dispersed in the liquid aldehyde stream in a manner known per se. In the interests of uniform liquid distribution, improved removal of heat of reaction and a high space-time yield, the reactors are preferably operated as high liquid throughputs of from 15 to 120 m$^3$, in particular from 25 to 80 m$^3$, per m$^2$ of cross section of the empty reactor an hour. If a reactor is operated isothermally and in a single pass, the space velocity over the catalyst (LHSV) can be from 0.1 to 10 h$^{-1}$. These ranges each independently include all values and subranges therebetween, including 16, 20, 30, 40, 50, 60, 70, 90, 100, 110 and 115 m$^3$, per m$^2$ of cross section of the empty reactor an hour; and 0.2, 0.5, 0.9, 1, 1.1, 2, 3, 4, 5, 6, 7, 8, and 9 h$^{-1}$.

In the hydrogenation of hydroformylation mixtures having from 8 to 17 carbon atoms, for example isononanal or tridecanal, preference is given to using a plurality of reactors connected in series. In this case, the first reactor is operated in the recirculation mode and the subsequent reactor(s) is(are) operated in the recirculation mode or in a single pass. As a reactor operated in the recirculation mode, it is possible to use, for example, a shaft oven with a heat exchanger in an external circuit or a shell-and-tube reactor.

To minimize secondary reactions and thus to increase the alcohol yield, it is advantageous to limit the aldehyde concentration in the feed to the reactor. Particularly in the hydrogenation of hydroformylation mixtures having from 8 to 17 carbon atoms, the aldehyde content in the reactor feed is from 1 to 35%, preferably from 5 to 25%. In the case of reactors operated in the recirculation mode, a concentration in the desired range can be set by means of the recirculation ratio (ratio of recirculated hydrogenation product to feed). These ranges include all values and subranges therebetween, including 9, 10, 11, 12, 13, 14, 15, and 16 carbons; 2, 3, 4, 6, 7, 8, 9, 10, 15, 20, 22, 26, 30, 31, 33%.

The process of the invention is carried out in a pressure range from 5 to 100 bar, in particular from 5 to 40 bar, particularly preferably in the range from 10 to 25 bar. The hydrogenation temperatures are in the range from 120 to 220° C., in particular from 140 to 190° C. These ranges independently include all values and subranges therebetween, including 6, 8, 9, 15, 20, 30, 35, 45, 50, 60, 70, 80, and 90 bar; and 130, 150, 160, 170, 180, 200, and 210° C.

The hydrogen necessary for the hydrogenation is preferably used in pure form in only a small excess, so that little water goes into the gas phase and is carried out with the latter. The amount of hydrogen fed into each reactor is from 103 to 150% of the amount consumed by reaction, in particular from 103 to 120%. In other words, the hydrogen consumed in the hydrogenation is replaced in an excess of from 3 to 50%, preferably from 3 to 20%, particularly preferably from 5 to 10%. These ranges each independently include all values and subranges therebetween, including 104, 105, 110, 115, 119, 121, 122, 125, 130, 135, 140, 145, 148 and 149% of the amount consumed by reaction; and 4, 6, 7, 8, 9, 11, 15, 20, 25, 30, 35, 40, 45, 48 and 49% for the the hydrogen consumed in the hydrogenation replaced in excess.

The hydrogenation product is preferably worked up by distillation. This is carried out at atmospheric pressure or under reduced pressure. In the case of high-boiling alcohols, i.e. $C_8$–$C_{16}$-alcohols, distillation under reduced pressure is preferred.

Other preferred embodiments of the present invention include downstream processes for preparing organic compounds, such as plasticizers and detergents. Preferred examples of downstream processes include esterification reaction between the product alcohol and phthalic acid (anhydride) to produce one or more plasticizer. Another example includes admixing the plasticizer and a polymer resin to produce an improved polymer composition.

Especially preferred alcohols include nonanols, decanols, dodecanols and tridecanols ($C_9$, $C_{10}$, $C_{12}$ and $C_{13}$ alcohols) either as pure compounds, mixtures, mixtures of isomers, and combinations thereof.

EXAMPLES

Having generally described this invention, a further understanding can be obtained by reference to certain specific examples which are provided herein for purposes of illustration only and are not intended to be limiting unless otherwise specified.

Example 1

Comparative Example

C9-Aldehyde Hydrogenation in the Liquid Phase/Water-Free Crude Aldehyde as starting Material One liter of crude reaction product from the Co-catalyzed hydroformylation of dibutene containing 1.15% by weight of water and 5.16% by weight of high boilers was subjected to a laboratory distillation to remove the water (down to 110 ppm of residual water) and then hydrogenated in the liquid phase in a circulation apparatus at 180° C. and 25 bar absolute over 100 g of a Cu/Cr/Ni catalyst on an $Al_2O_3$ support. The amount of off gas was 1 standard 1/h. The analyses of starting material and product are shown in table 1.

TABLE 1

| Running time (hours) | C8-hydrocarbon (% by weight) | C9-aldehyde (% by weight) | Formate (% by weight) | C9-alcohol (% by weight) | High boilers (% by weight) |
|---|---|---|---|---|---|
| 0 | 9.32 | 46.50 | 3.24 | 35.79 | 5.16 |
| 1 | 9.28 | 0.29 | 1.35 | 83.64 | 5.44 |
| 2 | 9.25 | 0.18 | 0.45 | 84.03 | 6.10 |
| 3 | 9.18 | 0.15 | 0.22 | 84.00 | 6.45 |

As can be seen from table 1, the high boilers are not cleaved, but are instead formed, when the hydrogenation of isononanal is carried out in the absence of water in the starting material.

Example 2

According to the Invention

C9-Aldehyde Hydrogenation/Water-Containing Crude Aldehyde as Starting Material

One liter of crude reaction product from the Co-catalyzed hydroformylation of dibutene containing 1.5% by weight of residual water and 5.35% by weight of high boilers was hydrogenated in the liquid phase in a circulation apparatus at 180° C. and 25 bar absolute over 100 g of a Cu/Cr/Ni catalyst on an $Al_2O_3$ support. The amount of offgas was 1 standard 1/h. The analyses of starting material and product are shown in table 2, calculated on an anhydrous basis.

TABLE 2

| Running time (hours) | C8-hydrocarbon (% by weight) | C9-aldehyde (% by weight) | Formate (% by weight) | C9-alcohol (% by weight) | High boilers (% by weight) |
|---|---|---|---|---|---|
| 0 | 9.12 | 47.2 | 3.16 | 37.17 | 5.35 |
| 1 | 9.18 | 0.34 | 0.32 | 85.72 | 4.45 |
| 2 | 9.15 | 0.20 | <0.01 | 86.67 | 3.84 |
| 3 | 9.09 | 0.18 | <0.01 | 86.86 | 3.73 |

As can be seen from table 2, part of the high boilers is cleaved to form products of value during the hydrogenation of crude isononanal in the presence of water in the starting material and the formates are reacted more rapidly and virtually quantitatively. After the hydrogenation, the liquid reaction mixture contains 1.01% by weight of water.

Example 3

According to the Invention

C9-Aldehyde Hydrogenation/Water-Containing Starting Material Low in High Boilers One liter of crude reaction product from the Co-catalyzed hydroformylation of dibutene containing 1.20% by weight of water was subjected to a laboratory distillation to substantially remove the high boilers (from 4.65% by weight down to 0.13% by weight) and then hydrogenated in the liquid phase in a circulation apparatus at 180° C. and 25 bar absolute over 100 g of a Cu/Cr/Ni catalyst on an $Al_2O_3$ support. The amount of offgas was 1 standard 1/h. The analyses of starting material and product are shown in table 3.

Example 4

Comparison

C9-Aldehyde Hydrogenation/Water-Free Starting Material Low in High Boilers

One liter of crude reaction product from the Co-catalyzed hydroformylation of dibutene was subjected to a laboratory distillation to remove the residual water (from 1% by weight to 150 ppm) and high boilers and hydrogenated in the liquid phase in a circulation apparatus at 180° C. and 25 bar absolute over 100 g of a Cu/Cr/Ni catalyst on an $Al_2O_3$ support. The amount of offgas was 1 standard 1/h. The analyses of starting material and product are shown in table 4.

TABLE 3

| Running time (hours) | C8-hydrocarbon (% by weight) | C9-aldehyde (% by weight) | Formate (% by weight) | C9-alcohol (% by weight) | High boilers (% by weight) |
|---|---|---|---|---|---|
| 0 | 7.40 | 52.86 | 3.44 | 36.17 | 0.13 |
| 1 | 7.27 | 0.26 | 0.18 | 90.83 | 1.46 |
| 2 | 7.29 | 0.21 | 0.01 | 90.87 | 1.48 |
| 3 | 7.32 | 0.19 | <0.01 | 90.86 | 1.49 |

As can be seen from table 3, the isononyl formates are very quickly converted into the desired product isononanol

TABLE 4

| Running time (hours) | C8-hydrocarbon (% by weight) | C9-aldehyde (% by weight) | Formate (% by weight) | C9-alcohol (% by weight) | High boilers (% by weight) |
|---|---|---|---|---|---|
| 0 | 6.95 | 51.50 | 3.64 | 37.79 | 0.13 |
| 1 | 6.97 | 0.33 | 1.21 | 87.05 | 4.44 |
| 2 | 6.98 | 0.19 | 0.50 | 89.21 | 3.13 |
| 3 | 6.94 | 0.15 | 0.27 | 89.63 | 3.01 | in the hydrogenation of isononanal in the presence of water dissolved homogeneously in the starting material.

The high boiler contents settle down to a constant value of about 1.46% by weight after a running time of one hour.

After the hydrogenation, the reaction mixture contains 0.70% by weight of water.

As can be seen from table 4, the isononyl formates are, in contrast to example 3, converted only slowly into the desired product isononanol in the hydrogenation of isononanal in the absence of water in the starting material. Furthermore, high boiler formation is significantly higher in the absence of water.

Obviously, numerous modifications and variations of the present invention are possible in light of the above teachings. It is therefore to be understood that within the scope of the appended claims, the invention may be practiced otherwise than as specifically described herein.

This application is based on German patent application 10062448.0, filed Dec. 14, 2000, the entire contents of which are hereby incorporated by reference, the same as if set forth at length.

What is claimed is:

1. A process, comprising:
in a homogeneous liquid phase comprising water, and over a fixed-bed catalyst,
continuously hydrogenating at least one hydroformylation product obtained directly from a hydroformylation of one or more $C_{4-16}$ olefins to produce at least one output mixture:
wherein said fixed-bed catalyst comprises at least one element of transition group eight of the Periodic Table of the Elements;
wherein said output mixture comprises at least one corresponding alcohol and from 0.05 to 10% by weight of water;
and wherein in a steady-state operation of the process, from 3 to 50% more hydrogen is fed to the hydrogenation than is consumed by the hydrogenation.

2. The process as claimed in claim 1, wherein said output mixture comprises from 0.5 to 8% by weight of water.

3. The process as claimed in claim 1, wherein said output mixture comprises from 1 to 5% by weight of water.

4. The process as claimed in claim 1, wherein the hydrogenation is carried out at a pressure of from 5 to 100 bar.

5. The process as claimed in claim 1, wherein the hydrogenation is carried out at a pressure of from 5 to 40 bar.

6. The process as claimed in claim 1, wherein the hydrogenation is carried out at a temperature of from 120 to 220° C.

7. The process as claimed in claim 1, wherein said fixed-bed catalyst comprises at least two metals selected from the group consisting of copper, chromium and nickel.

8. The process as claimed in claim 1, wherein said fixed-bed catalyst comprises copper, chromium and nickel.

9. The process as claimed in claim 1, wherein said fixed-bed catalyst comprises:
from 0.3 to 15% by weight of copper;
from 0.3 to 15% by weight of nickel;
from 0.05 to 3.5% by weight of chromium; and
from 0 to 1.6% by weight of an alkali metal.

10. The process as claimed in claim 1, wherein said fixed-bed catalyst comprises at least one support material selected from the group consisting of silicon dioxide, aluminum oxide, and mixtures thereof.

11. The process as claimed in claim 1, wherein said hydroformylation product comprises one or more aldehydes in an amount of 1 to 35% by weight of said homogeneous liquid phase.

12. The process as claimed in claim 1, wherein said hydroformylation product comprises one or more aldehydes in an amount 5 to 20% by weight of said homogeneous liquid phase.

13. The process as claimed in claim 1, wherein said hydroformylation product is obtained from a hydroformylation of at least one selected from the group consisting of $C_8$-olefins and $C_8$-olefin mixtures.

14. The process as claimed in claim 1, wherein said hydroformylation product is obtained from a hydroformylation of at least one selected from the group consisting of $C_{12}$-olefins or $C_{12}$-olefin mixtures.

15. The process as claimed in claim 1, wherein said hydroformylation product is obtained from a hydroformylation of at least one selected from the group consisting of 1-butene, 2-butene, isobutene, 1- or 2-pentene, 2-methyl-1-butene, 2 methyl-2-butene, 3-methyl-1-butene, 1-, 2- or 3-hexene, C6-olefin mixture obtained in the dimerization of propene (dipropene), heptene, 2- or 3 methyl-1-hexene, octene, 2-methylheptene, 3-methylheptene, 5-methyl-2-heptene, 6-methyl-2-heptene, 2-ethyl-1-hexene, mixture of isomeric C8-olefins obtained in the dimerization of butenes, dibutene, nonene, 2- or 3-methyloctene, C9-olefin mixture obtained in the trimerization of propene, tripropene, decene, 2-ethyl-1-octene, dodecene, C12-olefin mixture obtained in the tetramerization of propene or the trimerization of butenes, tetrapropene, tributene, tetradecene, pentadecene, hexadecene, C16-olefin mixture obtained in the tetramerization of butenes, tetrabutene, and mixtures thereof.

16. The process as claimed in claim 1, further comprising, prior to the hydrogenation, separating said hydroformylation product by distillation.

17. The process as claimed in claim 1, wherein said element in said fixed-bed catalyst is selected from the group consisting of Fe, Ru, Os, Co, Rh, Ir, Ni, Pd, Pt, and mixtures thereof.

18. The process as claimed in claim 1, further comprising distilling said output mixture.

19. The process as claimed in claim 1, wherein said alcohol is a high-boiling alcohol.

20. The process as claimed in claim 1, wherein said alcohol is selected from the group consisting of $C_9$, $C_{10}$, $C_{12}$, $C_{13}$ alcohol, and mixtures thereof.

* * * * *

UNITED STATES PATENT AND TRADEMARK OFFICE
CERTIFICATE OF CORRECTION

PATENT NO. : 6,680,414 B2
DATED : January 20, 2004
INVENTOR(S) : Knoop et al.

It is certified that error appears in the above-identified patent and that said Letters Patent is hereby corrected as shown below:

<u>Title page,</u>
Item [30], Foreign Application Priority Data, should read:
-- [30]  Foreign Application Priority Data
  Dec. 14, 2000  (DE) ……………………….. 100 62 448 --

Signed and Sealed this

Sixth Day of April, 2004

JON W. DUDAS
*Acting Director of the United States Patent and Trademark Office*